United States Patent [19]
Lee et al.

[11] Patent Number: 4,977,246
[45] Date of Patent: Dec. 11, 1990

[54] HIGH RECOVERY PROCESS FOR ANTIHEMOPHILIC FACTOR

[75] Inventors: Ted C. K. Lee, Lansdale; Michael E. Hrinda, Gwynedd Valley, both of Pa.

[73] Assignee: Rorer Pharmaceutical Corporation, Fort Washington, Pa.

[21] Appl. No.: 361,885

[22] Filed: Jun. 6, 1989

[51] Int. Cl.$^5$ .......................... C07K 3/24; C07K 3/28; C07K 3/18
[52] U.S. Cl. .................................. 530/383; 530/412; 530/415; 530/418; 530/419
[58] Field of Search ............... 530/383, 412, 415, 418, 530/419

[56] References Cited

U.S. PATENT DOCUMENTS 2,867,567  1/1959  Bidwell .
3,920,625  11/1975 Andersson et al. ................ 530/383
3,973,002  8/1976  Hagan et al. .
4,383,989  5/1983  Rock .

OTHER PUBLICATIONS

Brinkhous et al., "A New High—Potency Glycine—Precipitated Anti—Hemophilic Factor (AHF) Concentrate", (JAMA, Aug. 26, 1988, vol. 205, No. 9).
Newman et al., "Methods for the Production of Clinically Effective Intermediate— and High—Purity Factor VIII Concentrates", (British Journal of Haemotology, 1971, 21, pp. 1-20).

Primary Examiner—Margaret Moskowitz
Assistant Examiner—Keith C. Furman
Attorney, Agent, or Firm—Imre (Jim) Balogh; James A. Nicholson

[57] ABSTRACT

Disclosed is a method of recovery of antihemophilic factor (AHF) from human plasma by precipitation with citric acid, sodium citrate, or potassium citrate.

6 Claims, No Drawings

HIGH RECOVERY PROCESS FOR ANTIHEMOPHILIC FACTOR

BACKGROUND OF THE INVENTION

1. Field of the Invention

This invention relates to a method for recovery of antihemophilic factor from human plasma. More particularly, the invention relates to the precipitation of human antihemophilic factor from plasma by a treatment with citric acid, sodium citrate or potassium citrate.

2. Description of the Prior Art

Hemostatis, the biochemistry of blood coagulation, is an extremely complex and as yet not completely understood phenomena whereby normal whole blood and body tissue prevent an excess loss of blood from a ruptured blood vessel. The total mechanism of blood coagulation is affected through the coordinated interaction of biochemical substances contained in three basic physiologic systems; namely, extravascular tissue such as subcutaneous tissue, muscle tissue, and skin; the blood vessel wall; and intravascular components, including blood plasma proteins, blood plasma factors, and platelets.

Hemophilia type A is a genetically induced disease characterized by the loss of clottability of otherwise normal whole blood. It is believed that a cause of hemophilia is the inability of the afflicted individual to synthesize, or produce sufficient quantities of the active form of antihemophilic factor, known as AHG, AHF, Factor VIII or Factor VIII:C (hereinafter AHF) to maintain adequate clotting. Although, at present, hemophilia cannot be cured, it can be treated therapeutically by the administration of AHF to an AHF-deficient patient. The administered AHF is derived from blood obtained from normal and healthy donors and is administered either by transfusion of whole blood or blood plasma, or by infusion of AHF plasma protein concentrate which has been extracted from the plasma of normal human whole blood.

The prior art describes various processes for obtaining AHF from human and animal plasma including separation from other proteins, concentration and purification, such as described in: U.S. Pat. Nos. 4,210,580; 4,361,509; 3,973,002; 4,383,989; and publications: Brinkhous et al, "A New High-Potency Glycine - Precipitated Antihemophilic Factor Concentrate, JAMA, Aug. 26, 1968, Vol 205, No. 9; Newman et al, "Methods for the Production of Clinically Effective Intermediate- and High-Potency Factor VIII Concentrates, British Journ. of Haemat., 1971, (21) 1-20; D. E. G. Austen, "The Chromatographic Separation of Factor VIII on Aminohexyl Sepharose", British Journ. of Haemat., 1979, (43) 669–674; Morgenthaler, "Chromatography of Antihemophilic Factor on Diaminoalkane- and Aminoalkane-Derivatized Sepharose", Thromb. Haemostas. 47 (2) 124–127 (1982); and Faure et al, "Improved Buffer for the Chromatographic Separation of Factor VIII Coagulant; J. Chromatography 257 (1983) 387–391. The object of the prior art is to develop highly purified, highly concentrated AHF preparations from a large quantity of pooled plasma. The high potency AHF concentrates are produced by first separating an AHF rich fraction from pooled plasma by means of Cohn's ethanol fractionation method or from cryoprecipitate obtained by freezing a plasma and then thawing it at low temperature, or from freshly obtained bovine, pig or sheep blood plasma by precipitating the AHF rich fraction with ethanol, ethyl ether, ammonium sulfate, amino acids, glycine and with phosphates or citrates, such as described in U.S. Pat. No. 2,867,567 to Bidwell.

Blood plasma is a scarce and expensive commodity due to limited avaiability of donors, collection and handling difficulties and cost of screening to avoid infectious diseases, such as hepatitis and AIDS. In order to best utilize such a resource and make AHF affordable to hemophiliacs, it is important to prevent losses thereof, during the process of obtaining the purified, therapeutically effective product. One of the most important steps in preventing loss of AHF occurs at separation/precipitation of the AHF-rich proteins from fresh blood or frozen plasma. Depending on the blood type of plasma and the particular methods of separation/precipitation used, recovery of AHF from normal human plasma has generally been in the range of from about 320 to 470 units per liter of plasma with AHF activity ranging from about 650 to about 1,400 units per liter of plasma.

The present invention is directed to a method by which higher recovery of AHF from human plasma is obtained using citric acid, sodium and potassium citrates as precipitants for the AHF-rich fraction.

SUMMARY OF THE INVENTION

The present invention is directed to a process for recovering AHF-rich fraction from human plasma comprising the steps of:

thawing plasma at a temperature of 6° C. to 10° C. to obtain a solution;

slowly adding with gentle mixing one volume of about 1.20 to 1.80 M solution of a precipitating agent, having a pH of about 7.1 to 8.2, selected from the group consisting of sodium citrate, potassium citrate and citric acid to two volumes of plasma solution at a temperature of about 0° C. to 10° C. to form a precipitate;

incubating the mixture in an ice bath for about 20 to 40 minutes;

separating the precipitate by centrifugation at a temperature of about 0° C. to 4° C. and at 10,000 xg for about 20 to 40 minutes; and collecting the Factor VII rich precipitate.

Optionally, the AHF-rich fraction can be dissolved in a buffer solution and then treated with aluminum hydroxide gel (Rehsorptar, 2% aluminum oxide gel) to adsorb the vitamin K dependent blood coagulation factors.

The AHF-rich fraction obtained by the method of the present invention contains about 500 to 800 units of AHF per liter of plasma with AHF activity in the range of about 650 to about 1,400 units per liter of plasma.

Except where otherwise indicated, AHF activity is measured by the following methods:

A sample of the Factor VIII-rich precipitate is dissolved in a buffer solution containing 20 mM histidine, 150 mM lysine hydrochloride and 0.15 M sodium chloride, at pH 7.0 and assayed for Factor VIII activity by the One-Stage Assay or Activated Partial Thromboplastin Time (APTT) method which is essentially as described by: (a) Hardisty, R. M. and MacPherson, J. C. (1962), Thrombosis at Diatheses Haemorrhagica, I, pp. 215–229, and (b) Zacharski, L. R. and Rosenstein, R. (1978) Am. J. Clin. Path. 70, pp. 280–286; or the two stage assay method which is essentially the same as the method described by Newman, J., Johnson, A. J. Karpatkin, S. and Puszkin, S. (1971), Br. J. Haematol. 21, pp. 1-20.

DETAILED DESCRIPTION OF THE INVENTION

It was discovered that by utilizing the method of the present invention, higher amounts of AHF-rich fractions can be recovered from human plasma as compared to heretofore used methods.

The starting material of the present invention is freshly frozen human plasma, which contains about 1/10 volume of 4% sodium citrate as an anticoagulant, is obtainable from plasma collection centers, such as Plasma Alliance, Inc., Knoxville, Tenn.

Other materials used in the practice of the invention may be obtained from the following sources: Sodium citrate and potassium citrate may be obtained from Mallinkrodt, Inc.; and citric acid may be obtained from Fischer Scientific Company.

Referring to the process described in Summary of the Invention, the freshly frozen plasma is thawed under controlled condition such that the temperature is maintained at about 6° C. to 12° C. during the thawing process. To the solubilized plasma one volume of a precipitating aqueous solution containing about 1.20 to 1.80 M precipitating agent of sodium citrate, potassium citrate, citric acid or a mixture thereof is added slowly, with mixing, to two volumes of the solubilized plasma while maintaining the temperature in the range of about 0° to 20° C. Accordingly, the final concentration of the precipitating agent in the solution is about 0.40 to 0.60 M. The pH of the solution should be about 7.1 to 8.2. The addition of the precipitating agent results in the formation of AHF-rich precipitate admixed with the solution.

The mixture is incubated in an ice bath to complete the precipitation reaction and to effect increased association of protein particles and consequent better separation of the precipitate.

Finally, the Factor VIII-rich precipitate is collected by centrifugation at around 0° to 6° C. and 10,000 xg for about 30 minutes.

After obtaining the Factor VIII-rich fraction, it is often convenient, but not necessary, to remove many of the trace proteins contained in the precipitate by various purification steps. One such procedure is the adsorbtion of blood Factors II, VII, IX and X and thromboplastin on an aluminum hydroxide gel (Rehsorptar, 2% aluminum oxide gel).

The AHF-rich fraction can be formulated in a buffer solution and lyophilized to produce a therapeutic quality product or may be further processed by using several standard laboratory techniques to produce a purer product. One such technique is monoclonal antibody column chromatography.

Following the chromatography, the column eluate may be formulated and lyophilized at −45° C. for 48 hours on a Hull lyophilizer.

The following examples will further illustrate the invention.

EXAMPLE 1

Precipitation of Factor VIII in Human Plasma with Sodium Citrate

Frozen human plasma, which contains 1/10±1/15 volume of 4% sodium citrate as an anticoagulant, was thawed in a 6° C. water bath. To 100 ml of the thawed plasma 50 ml of 1.57 M sodium citrate, at pH 7.1 and at 0° C., was added. The mixture was incubated in an ice bath for 30 minutes. The precipitate formed was separated from the supernatant by centrifugation at 4° C. and 10,000 xg for 30 minutes. The precipitate was dissolved in 50 ml of a buffer (20 mM histidine, 100 mM lysine hydrochloride, 150 mM sodium chloride, pH 7.0) and assayed for Factor VIII activity. The protein content in the dissolved precipitate was determined by a dye binding method of Bradford (Bradford, M., Anal. Biochem., 72, 248 (1976)). Result is shown in Table I.

TABLE I

|  | Human Plasma | Citrate Derived Precipitate Dissolved in Buffer |
|---|---|---|
| Volume (ml) | 100 | 56 |
| Activity (u/ml) | 0.99 | 1.2 |
| Total Activity (u) | 99 | 67 |
| Yield (% w/v) | 100 | 68 |
| Protein (mg/ml) | 90 | 15 |
| Factor VIII (u/mg protein) | 0.01 | 0.08 |
| Purification (fold) | — | 8 |

In a control experiment, the incubation step at 0° C. was omitted and the plasma-sodium citrate mixture was centrifuged at 10,000 xg for 30 minutes to collect the precipitate. The yield of AHF in the precipitate was about 30%.

In another control experiment, the thawed plasma was incubated in an ice bath for 30 minutes and then the plasma was centrifuged at 10,000 xg for 30 minutes. The AHF yield in the precipitate was only 10%.

Example 2 and Table II are included for comparative purposes.

EXAMPLE 2

Precipitation of Factor VIII in Human Plasma by the Bidwell Process (U.S. Pat. No. 2,867,567) (Comparative Example)

The thawed human plasma of Example 1 was used. To 100 ml of human plasma, 5 ml of aluminum hydroxide gel was added and the mixture was incubated at room temperature for 15 minutes to adsorb the prothrombin complexes. The mixture was centrifuged at 4° C. and 2,000 xg for 10 minutes to separate the supernatant from the precipitate. The supernatant was mixed with an equal volume of 0.68 M sodium citrate at pH 6.5 and at 0° C., and the mixture was centrifuged to collect the precipitate. The precipitate was dissolved and the protein content was determined as in Example 1. The result is shown in Table II.

TABLE II

|  | Human Plasma | Resulting Precipitate Dissolved in Buffer |
|---|---|---|
| Volume (ml) | 100 | 51 |
| Activity (u/ml) | 0.99 | 0.34 |
| Total Activity (u) | 99 | 17 |
| Yield (% w/v) | 100 | 17 |
| Factor VIII (u/mg protein) | 0.01 | 0.11 |
| Purification (fold) | — | 11 |

Comparing Tables I and II, it is to be noted that while the Bidwell process achieves an 11-fold purification, it only reaches a 17% yield; the process of the present invention results in an 8-fold purification and a 68% yield.

Example 3 illustrates recovery results obtained using blood types A, B and O.

EXAMPLE 3

Recovery of Factor VIII from Human Plasma, Blood Types A, B and O, by Precipitation with Sodium Citrate Human plasmas having blood types A, B and O were treated with sodium citrate according to the method described in Example 1. The results are summarized in Tables III, IV and V.

TABLE III

Recovery of Factor VIII from Plasma Type A by Precipitation with Sodium Citrate*

| | Plasma | | | Suspended ppt. | | | Recovery | |
|---|---|---|---|---|---|---|---|---|
| | u/ml | Wgt (g) | Total (u) | u/ml | Wgt (g) | Total (u) | % | u/l plasma |
| Experiment #1 | 0.96 | 10 | 9.6 | 0.80 | 10 | 8 | 83 | 800 |
| Experiment #2 | 0.88 | 750 | 660 | 2.1 | 212 | 444 | 67 | 592 |
| Experiment #3 | 0.82 | 700 | 574 | 2.61 | 201 | 524 | 91 | 749 |
| Experiment #4 | 0.98 | 750 | 735 | 2.31 | 252 | 582 | 79 | 776 |
| Experiment #5 | 0.65 | 750 | 488 | 1.77 | 209 | 369 | 78 | 492 |
| Experiment #6 | 0.82 | 750 | 615 | 2.55 | 220 | 561 | 91 | 748 |
| Average | 0.85 | — | — | — | — | — | 82 | 693 |

*0.52M, based on total volume of plasma and sodium citrate solutions

TABLE IV

Recovery of Factor VIII from Plasma Type B by Precipitation with Sodium Citrate*

| | Plasma | | | Factor VIII Soln. | | | Recovery | |
|---|---|---|---|---|---|---|---|---|
| | u/ml | Wgt (g) | Total (u) | u/ml | Wgt (g) | Total (u) | % | u/l plasma |
| Experiment #1 | 1.28 | 750 | 960 | 2.25 | 229 | 514 | 54 | 685 |
| Experiment #2 | 1.40 | 350 | 490 | 2.66 | 106 | 282 | 58 | 806 |
| Experiment #3 | 0.78 | 20 | 15.6 | 1.21 | 11.3 | 13.6 | 87 | 680 |
| Experiment #4 | 1.80 | 120 | 216 | 3.54 | 35 | 124 | 57 | 1,033 |
| Experiment #5 | 1.42 | 300 | 426 | 2.02 | 107 | 216 | 51 | 720 |
| Average | 1.34 | — | — | — | — | — | 61 | 785 |

*0.52M, based on total volume of plasma and sodium citrate solutions

TABLE V

Recovery of Factor VIII from Plasma Type O by Precipitation with Sodium Citrate*

| | Plasma | | | Suspended ppt. | | | Recovery | |
|---|---|---|---|---|---|---|---|---|
| | u/ml | Wgt (g) | Total (u) | u/ml | Wgt (g) | Total (u) | % | u/l plasma |
| Experiment #1 | 0.97 | 700 | 679 | 1.95 | 229 | 447 | 66 | 639 |
| Experiment #2 | 0.93 | 750 | 698 | 1.53 | 225 | 344 | 49 | 459 |
| Experiment #3 | 0.89 | 360 | 320 | 1.50 | 107 | 161 | 50 | 445 |
| Experiment #4 | 0.82 | 700 | 574 | 1.62 | 218 | 353 | 62 | 505 |
| Average | 0.90 | — | — | — | — | — | 57 | 512 |

*0.52M, based on total volume of plasma and sodium citrate solutions

Samples generated by the method described in Example 1 were assayed for Factor VIII by the one-stage and two-stage assay methods referred to earlier, pre- and post-aluminum hydroxide gel treatment. The assay values of each sample are essentially the same, within experimental error. Examples of recovery values are shown in Table VI.

TABLE VI

One-Stage and Two-Stage Assays of Factor VIII Samples Generated by Sodium Citrate Treatment of Plasma

| | Pre-Al(OH)$_3$ Treatment | | Post-Al(OH)$_3$ Treatment | |
|---|---|---|---|---|
| Experiment # | 2-stage u/ml | 1-stage u/ml | 2-stage u/ml | 1-stage u/ml |
| 1 | 1.2 | 1.2 | — | — |
| 2 | 1.5 | 1.4 | 1.3 | 1.7 |
| 3 | 2.1 | 2.0 | 2.1 | 2.0 |
| 4 | 3.2 | 3.2 | 3.4 | 2.9 |

EXAMPLE 5

The Effect of Precipitating Agent's Concentration on The Precipitation of Factor VIII in Plasma The concentration of sodium citrate was varied between 0.10 M and 0.59 M in the precipitation process according to the present invention under the conditions described in Example 1. The optimum concentration of sodium citrate in the citrate-plasma mixture was at or about 0.52 M. Results are shown in Table VII.

TABLE VII

The Effect of Precipitating Agent's Concentration on The Precipitation of Factor VIII in Plasma

| Sodium Citrate Concentration M | Factor VIII Recovery u/ml |
|---|---|
| 0.59 | 0.71 |
| 0.52 | 0.80 |
| 0.39 | 0.60 |
| 0.20 | 0.28 |

TABLE VII-continued

The Effect of Precipitating Agent's Concentration on The Precipitation of Factor VIII in Plasma

| Sodium Citrate Concentration M | Factor VIII Recovery u/ml |
| --- | --- |
| 0.10 | 0.11 |

Similar recovery results were obtained with citric acid and potassium citrate in the concentration range of about 0.45 to 0.55 M.

EXAMPLE 6

The Effect of Temperature of the Precipitating Agent on Factor VIII Recovery

The temperature effect of 1.57 M sodium citrate solution at pH 7.1 on Factor VIII recovery from human plasma was studied by comparing Factor VIII recovery at 0° C. and 25° C. according to the process described in Example 1. Four samples were processed and tested at each of the temperatures. The average results were as shown:

Factor VIII recovery at 0° C.: 650 u/liter

Factor VIII recovery at 25° C.: 490 u/liter

EXAMPLE 7

The Effect of Freezing-Thawing of Factor VIII Activity in the Citrate-Derived Precipitate Factor VIII-rich precipitates were obtained by the method of Example 1. The wet precipitates were frozen at −70° C. for 2 weeks and then 3 weeks followed by thawing and assaying for Factor VIII activity. The results obtained showed that Factor VIII activity was maintained during the freezing-thawing process. Table VIII illustrates this finding.

TABLE VIII

Effect of Freezing on Factor VIII Activity in the Precipitate of Citrate Treated Plasma

| Experiment # | Pre-Freezing (u/g) | Post-Freezing (u/g) | Recovery % |
| --- | --- | --- | --- |
| 1 | 15.4 | 15.9 | 103 |
| 2 | 6.9 | 6.4 | 92 |

It should be understood by those skilled in the art that various modifications may be made in the present invention without departing from the spirit and scope thereof as described in the specification and defined in the appended claims.

What is claimed is:

1. A method for obtaining an AHF-rich product from human plasma comprising the steps of:
   (a) thawing freshly frozen human plasma at a temperature of 6° C. to 10° C. to obtain a plasma solution;
   (b) adding one volume of about 1.20 M to 1.80 M aqueous solution of a precipitating agent selected from the group consisting of sodium citrate, potassium citrate and citric acid to two volumes of said plasma solution obtained in step (a) at a temperature of about 0° C. to 10° C. to form a precipitate;
   (c) incubating the precipitate-containing solution in an ice bath for about 20 to 40 minutes; and
   (d) separating the precipitate from the solution.

2. The method of claim 1 further comprising the step of contacting said precipitate obtained in step (d) with aluminum hydroxide gel to remove vitamin K dependent coagulation factors therefrom.

3. The method of claim 1 wherein said aqueous solution of said precipitating agent has a pH of about 7.1 to 8.2.

4. The method of claim 1 wherein said separating of the precipitate is by centrifugation at a temperature of about 0° C. to 4° C. at 10,000 xg for 20 to 40 minutes.

5. The method of claim 1 wherein the concentration of the precipitating agent is about 0.40 M to 0.60 M based on the combined volume of the plasma solution and the aqueous solution containing the precipitating agent.

6. The method of claim 5 wherein the concentration of the precipitating agent is about 0.45 M to 0.55 M based on the combined volume of the plasma solution and the aqueous solution containing the precipitating agent.

* * * * *